(12) United States Patent
Terajima et al.

(10) Patent No.: US 8,436,055 B2
(45) Date of Patent: May 7, 2013

(54) MODIFIED ACIDIC ION-EXCHANGE RESIN AND METHOD FOR PREPARING BISPHENOL

(75) Inventors: Takashi Terajima, Sodegaura (JP); Toshihiro Takai, Sodegaura (JP); Kenji Fujiwara, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 114 days.

(21) Appl. No.: 12/875,016

(22) Filed: Sep. 2, 2010

(65) Prior Publication Data

US 2010/0324341 A1 Dec. 23, 2010

Related U.S. Application Data

(62) Division of application No. 10/951,725, filed on Sep. 29, 2004, now abandoned.

(30) Foreign Application Priority Data

Sep. 30, 2003 (JP) .................. 2003-339944
Apr. 28, 2004 (JP) .................. 2004-133344

(51) Int. Cl.
*C08J 5/20* (2006.01)

(52) U.S. Cl.
USPC .................. 521/25; 521/30; 568/11; 568/728

(58) Field of Classification Search .................. 521/25, 521/30; 568/11, 728
See application file for complete search history.

(56) References Cited

U.S. PATENT DOCUMENTS

| | | | |
|---|---|---|---|
| 4,303,551 A | 12/1981 | Vaughan | |
| 4,629,710 A | 12/1986 | Smith, Jr. | |
| 5,395,857 A | 3/1995 | Berg et al. | |
| 5,589,517 A | 12/1996 | Sugawara et al. | |
| 6,017,969 A * | 1/2000 | Jones et al. | 521/32 |
| 6,281,400 B1 | 8/2001 | Harmer et al. | |
| 6,414,200 B1 | 7/2002 | Spivack et al. | |
| 2002/0065438 A1 | 5/2002 | Gracey | |
| 2002/0123656 A1 | 9/2002 | Spivack | |
| 2004/0127753 A1 | 7/2004 | Iwahara et al. | |
| 2005/0070615 A1 * | 3/2005 | Terajima et al. | 521/25 |

FOREIGN PATENT DOCUMENTS

| | | |
|---|---|---|
| EP | 1 097 915 A1 | 5/2001 |
| JP | 6-320009 A | 11/1994 |
| JP | 6-340563 A | 12/1994 |
| JP | 7-47281 A | 2/1995 |
| JP | 08-089819 * | 4/1996 |
| JP | 08-187436 * | 7/1996 |
| JP | 8-187436 A | 7/1996 |
| JP | 10-211433 * | 8/1998 |
| JP | 10-337484 A | 12/1998 |
| JP | 2001-122610 A | 5/2001 |
| JP | 2002-316962 A | 10/2002 |
| TW | 200301159 A | 7/2003 |
| WO | WO 00/00454 A1 | 1/2000 |
| WO | WO 02/50000 A1 | 6/2002 |
| WO | WO 02/085830 A1 | 10/2002 |

* cited by examiner

*Primary Examiner* — Peter D. Mulcahy
*Assistant Examiner* — Henry Hu
(74) *Attorney, Agent, or Firm* — Birch, Stewart, Kolasch & Birch, LLP

(57) ABSTRACT

The present invention provides an ion-exchange resin catalyst, as a catalyst for preparing bisphenol from phenol compounds and ketone, which has a higher selectivity to bisphenol and a longer life time, as compared to a conventional ion-exchange resin, and a method for preparing the same.

The present invention also provides a method for preparing bisphenol comprising reacting phenol compounds with ketone, wherein the modified acidic ion-exchange resin in which at least one kind of cationic compound selected from the following (a), (b), (c) and (d) ionically binds to an acidic functional group, is used as a catalyst: (a) a quaternary phosphonium ion, (b) a quaternary ammonium ion, (c) a bis(phosphoranylidene) ammonium ion, and (d) an N-substituted nitrogen-containing aromatic cation.

4 Claims, No Drawings

US 8,436,055 B2

MODIFIED ACIDIC ION-EXCHANGE RESIN AND METHOD FOR PREPARING BISPHENOL

This application is a divisional application which claims priority under 35 U.S.C. 120 to U.S. application Ser. No. 10/951,725 filed on Sep. 29, 2004 now abandoned, which claims priority to Application No. 2003-339944 filed in Japan, on Sep. 30, 2003 and Application No. 2004-133344 filed in Japan on Apr. 28, 2004. All of which are hereby expressly incorporated by reference into the present application in their entirety.

TECHNICAL FIELD

The present invention relates to a modified acidic ion-exchange resin catalyst and a method for preparing bisphenol using the same. In particular, the present invention relates to a modified ion-exchange resin catalyst having a high reactive selectivity and a method for preparing bisphenol which comprises reacting phenol compounds with ketone and/or aldehyde in the presence of the catalyst.

BACKGROUND ART

Bisphenol A [2,2-bis(4-hydroxyphenyl)propane] is usually prepared by reacting phenol with acetone in the presence of a homogeneous acid or a solid acid catalyst. The phenol, water and other by-products formed by the reaction, in addition to bisphenol A. The main component of the by-products is 2-(2-hydroxyphenyl)-2-(4-hydroxyphenyl)propane (hereinafter, referred to as o,p'-BPA), and in addition, it includes trisphenol, a polyphenol compound, a chroman compound and colored impurities.

Examples of a homogeneous acid to be used as a catalyst, includes hydrochloric acid and sulfuric acid. In the case where the homogeneous acid is used, since it is possible to proceed the reaction while precipitating crystals of an adduct of phenol with bisphenol A by reacting them at lower temperatures, bisphenol A can be prepared with a high conversion of acetone and a high selectivity by decreasing the amount of the by-produced o,p'-BPA as an isomer thereof. However, the homogeneous acid such as hydrochloric acid requires removal of the catalyst from a reaction mixture or neutralization of the reaction mixture, and thus the process becomes complicated. Homogeneous dissolution of the acid in the reaction solution further causes corrosion of apparatus used in the reaction. Therefore, the reaction apparatus vessels should be made of expensive, anti-corrosive materials, thus being uneconomical.

As a solid acid catalyst, a sulfonic acid-type cation-exchange resin is usually used. The reaction for preparing bisphenol A essentially proceeds only with an acid catalyst, but if such a solid acid catalyst is used, the process in which acetone diffuses from the surface of the catalyst particles to an active site on the catalyst is involved, and thus the reaction rate is lowered. Thus, generally a method for improving the catalytic activity and the selectivity comprises allowing a compound containing a mercapto group to coexist in the reaction system. Specifically, there may be mentioned a method for passing a free type of a compound containing a mercapto group, such as alkylmercaptan together with phenyl and acetone as raw materials, through a fixed bed reactor filled with a sulfonic acid-type cation-exchange resin (Japanese Examined Patent Application Publication No. 45-10337, U.S. Pat. No. 6,414,200), a method for covalently binding a part of sulfonic acid groups of the sulfonic acid-type cation-exchange resin with a compound containing a mercapto group, and a method for ionically binding a part of sulfonic acid groups in a sulfonic acid-type cation-exchange resin with a compound containing a mercapto group (Japanese Examined Patent Application Publication No. 46-19953). In the method for passing a free type of a compound containing a mercapto group, such as alkylmercaptan together with phenol and acetone as raw materials, through the fixed bed reactor filled with a sulfonic acid-type cation-exchange resin, since a certain amount of a compound containing a mercapto group is usually allowed to exist in the reaction system, the compound containing a mercapto group may cause the coloration of bisphenol A, although it is advantageous in that deterioration of the catalyst is small. Thus, the compound containing a mercapto group should be removed and recovered. On the other hand, in the method for binding a part of the sulfonic acid groups in a sulfonic acid-type cation-exchange resin with a compound containing a mercapto group, it is advantageous in that the loss of the compound containing a mercapto group is small, and thus it is not necessary to recover the compound containing a mercapto group, as compared to the method wherein a free type of a compound containing a mercapto group exists in the reaction system. In particular, Japanese Unexamined Patent Application Publication Nos. 08-187436, 08-089819 and 10-211433 describe that a sufficient reaction rate of acetone is obtained by modifying the structure of a compound containing a mercapto group which binds to a strongly acidic ion-exchange resin.

On the other hand, for example, it has also been reported that the activity of a sulfonic acid-type cation-exchange resin as an acid catalyst is improved, which has been lower than that of the previously described homogeneous acid. First, in the case where a particle diameter of a sulfonic acid-type cation-exchange resin to be used is large, since the reaction raw materials do not sufficiently diffuse within the particles, a sufficient conversion of acetone is not obtained. Thus, Japanese Unexamined Patent Application Publication No. 62-178532 proposes to use the fine particles having an effective diameter of 0.3 mm or less, or the fine-powdered sulfonic acid-type cation-exchange resin. Further, Japanese Unexamined Patent Application Publication No. 6-340563 likewise provides a particle diameter of a sulfonic acid-type cation-exchange resin to be used and the distribution degree of the particle diameter and specifies a more preferred range thereof. Further, Japanese Unexamined Patent Application Publication Nos. 4-268316 and 2002-253971 describe a method for forming a sulfonic acid-type cation-exchange resin product having a desired particle diameter. As such, the particle diameter of a sulfonic acid-type cation-exchange resin is an important factor in obtaining a sufficient reaction conversion.

In addition, various kinds of improvements on the structure of a resin product which is a base material of a sulfonic acid-type cation-exchange resin have been made. The sulfonic acid-type cation-exchange resin is a resin obtained by sulfonating a styrene-divinylbenzene copolymer which is obtained by radically copolymerizing styrene and divinylbenzene. The divinylbenzene in polymerization does not only prevent a polystyrene chain from dissolving in an organic solvent, but also it is an important factor in controlling the size of a pore (a gel micropore) of the sulfonic acid-type cation-exchange resin formed by capturing a polar solvent by its content, or the mechanical strength of the sulfonic acid-type cation-exchange resin. In other words, a sulfonic acid-type cation-exchange resin with a low content of divinylbenzene has a high catalytic activity due to a large gel micropore, but the mechanical strength is low. In addition, in the case where the content thereof is high, the mechanical strength increases, but the gel micropore size decreases, which causes decreased activity. For an ion-exchange resin of which the degree of crosslinking becomes increased by increasing the content of divinylbenzene, there may be mentioned one which forms a large hole having a size of 20 nm or more, referred to as a "macropore" within the particles by a physical treatment in order to improve the diffusion within the particles.

However, in the case where an ion-exchange resin having macropores adsorbs molecules having high polarity, such as water, a crosslinked structure tends to inhibit the bulge of particles caused by the swelling, which eventually collapses when it can no longer endure the pressure from the swelling. Japanese Unexamined Patent Application Publication Nos. 5-97741 and 6-320009 describes a method which complements the respective defects by simultaneously filling a sulfonic acid-type cation-exchange resin having a low content of divinylbenzene and a sulfonic acid-type cation-exchange resin having a high content of divinylbenzene into a reactor. Further, WO 2000/00454 (Nippon Steel Chemical Co., Ltd.) reports an improvement on a reaction conversion, suggesting a sulfonic acid-type cation-exchange resin having large gel micropores by using large molecules such as divinylbiphenyl instead of divinylbenzene.

As such, various technologies have been examined for the catalyst, but none has been satisfactory with respect to the selectivity. Even when the activity decreases slightly, if it is possible to develop a catalyst having a high selectivity, the loading of the a by-product recovering process can be reduced in the preparation process and a phenol/acetone ratio as raw materials can be reduced by elevating the reaction temperature without deteriorating the selectivity, and thus the cost for recovering the phenol can be largely reduced. Here, the reduced level of the activity can be compensated by increasing the reactor size, wherein the increase in cost in the preparation of bisphenol is extremely small. Further, in view of the industrial applications, it is desirable to improve the life of catalysts. Therefore, the development of a catalyst having a high selectivity and a long life time is demanded.

[Patent Document 1] U.S. Pat. No. 6,414,200
[Patent Document 2] Japanese Unexamined Patent Application Publication No. 08-089819

DISCLOSURE OF THE INVENTION

An object of the present invention is to provide an ion-exchange resin catalyst which has a higher selectivity to bisphenol, as compared to conventional ion-exchange resins, used in a method for preparing bisphenol by reacting phenol compounds with ketone and a method for preparing the same.

The present inventors have conducted extensive studies to solve the problems, and as a result, they have found that by using, as a catalyst, an acidic ion-exchange resin in which at least one kind of cationic compound selected from compounds represented by the formulae (1), (2) and (3), and an N-substituted nitrogen-containing aromatic compound, ionically binds to an acidic functional group of the acidic ion-exchange resin, the selectivity to bisphenol can be increased and the activity or the selectivity of a catalyst can also be maintained for a longer period of time, and accordingly bisphenol can be obtained with a high yield. Thus, they have completed the present invention.

In other words, the present invention provides an acidic ion-exchange resin which is neutralized with at least one kind of cationic compound selected from the compounds represented by the formulae (1), (2) and (3), and an N-substituted nitrogen-containing aromatic compound, a catalyst comprising the ion-exchange resin, and a method for preparing bisphenol using the catalyst.

BEST MODE FOR CARRYING OUT THE INVENTION

As an ion-exchange resin used in the present invention, an acidic ion-exchange resin is preferable, and it includes, for example, one in which a sulfone group is introduced into a styrene-divinylbenzene copolymer which is referred to as a general strongly acidic ion-exchange resin and a perfluoroalkyl sulfonic acid-based resin such as Nafion.

A modified acidic ion-exchange resin according to the present invention can be obtained by ionically binding at least one kind of cationic compound selected from the least one kind of cationic compound selected from the compounds represented by the formulae (1), (2) and (3) and an N-substituted nitrogen-containing aromatic compound to an acidic ion-exchange resin.

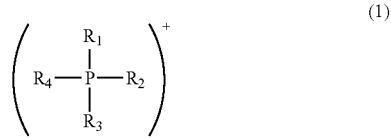

wherein P represents a phosphorus atom; and $R_1$, $R_2$, $R_3$ and $R_4$ independently represent a hydrogen atom, or an alkyl group, an aryl group or an alkoxy group, each of which contains 1 to 20 carbon atoms and does not contain any of a mercapto group and a precursor thereof, provided that at least one of $R_1$, $R_2$, $R_3$ and $R_4$ is a group other than a hydrogen atom, that is, a phosphonium ion, $PH_4^+$ is excluded;

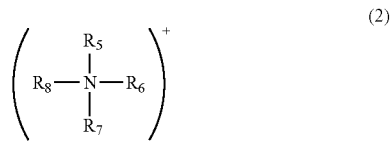

wherein N represents a nitrogen atom; and $R_5$, $R_6$, $R_7$ and $R_8$ independently represent an alkyl group or an aryl group, each of which contains 1 to 20 carbon atoms and does not contain any of a mercapto group, a precursor thereof and an amide bond; and

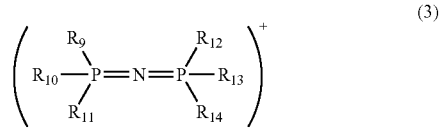

wherein P represents a phosphorus atom; and $R_9$, $R_{10}$, $R_{11}$, $R_{12}$, $R_{13}$ and $R_{14}$ independently represent a hydrogen atom or an alkyl group, an aryl group or an alkoxy group, each of which contains 1 to 20 carbon atoms and does not contain a mercapto group and/or a precursor thereof, provided that at least one of $R_9$, $R_{10}$, $R_{11}$, $R_{12}$, $R_{13}$ and $R_{14}$ is a group other than a hydrogen atom.

When the ion-exchange resin is modified with the cationic compound represented by the formula (1), a method for ionexchanging an acidic functional group of the ion-exchange resin with the cationic compound represented by the formula (1) can be used, but a neutrally charged compound represented by the formula (4) as a precursor, may be also brought into contact with the acidic ion-exchange resin for cationization.

(4)

wherein P represents a phosphorus atom; and $R_{15}$, $R_{16}$ and $R_{17}$ independently represent a hydrogen atom, or an alkyl group, an aryl group or an alkoxy group, each of which contains 1 to 20 carbon atoms and does not contain any of a mercapto group and a precursor thereof, provided that at least one of $R_{15}$, $R_{16}$ and $R_{17}$ is a group other than a hydrogen atom, that is, phosphine, $PH_3$ is excluded.

The cationic compound represented by the formula (1), which is used in the present invention, is the compound wherein P represents a phosphorus atom; and $R_1$, $R_2$, $R_3$ and $R_4$ independently represent a hydrogen atom, or an alkyl group, an aryl group or an alkoxy group, each of which contains 1 to 20 carbon atoms, preferably 1 to 16 carbon atoms, and more preferably 1 to 12 carbon atoms and does not contain any of a mercapto group and a precursor thereof, and at least one of $R_1$, $R_2$, $R_3$ and $R_4$ represents an alkyl group, an aryl group or an alkoxy group, each of which contains 1 to 20 carbon atoms, preferably 1 to 16 carbon atoms, and more preferably 1 to 12 carbon atoms and does not contain any of a mercapto group and a precursor thereof. The expression "independently" indicates that $R_1$, $R_2$, $R_3$ and $R_4$ may be the same or different in structure. The structures of $R_1$, $R_2$, $R_3$ and $R_4$ are not particularly limited to other structures, if they do not contain any of a mercapto group and a precursor thereof. They may contain a functional group such as an amino group, an ammonium group, a carbonyl group, a carboxyl group, a sulfonyl group, a sulfone group, a hydroxyl group, a nitrile group, a nitro group and an alkoxy group, and a halogen atom. Further, $R_1$, $R_2$, $R_3$ and $R_4$ may bind with each other to form a ring. In addition, a precursor of a mercapto group indicates a mercapto group-producing precursor, for example, such as thiazolidines, thioethers and disulfides.

The cationic compound represented by the formula (2), which is used in the present invention, is the compound wherein N represents a nitrogen atom; and $R_5$, $R_6$, $R_7$ and $R_8$ independently represent a hydrogen atom, or an alkyl group, an aryl group or an alkoxy group, each of which contains 1 to 20 carbon atoms, preferably 1 to 16 carbon atoms, and more preferably 1 to 12 carbon atoms and does not contain any of a mercapto group, a precursor thereof and an amide bond, and at least one of $R_5$, $R_6$, $R_7$ and $R_8$ represents an alkyl group, an aryl group or an alkoxy group, each of which contains 1 to 20 carbon atoms, preferably 1 to 16 carbon atoms, and more preferably 1 to 12 carbon atoms and does not contain any of a mercapto group, a precursor thereof and an amide bond. The expression "independently" indicates that $R_5$, $R_6$, $R_7$ and $R_8$ may be the same or different in structure. The structures of $R_5$, $R_6$, $R_7$ and $R_8$ are not particularly limited to other structures, if they do not contain any of a mercapto group, a precursor thereof and an amide bond. They may contain a functional group such as an amino group, an ammonium group, a carbonyl group, a carboxyl group, a sulfonyl group, a sulfone group, a hydroxyl group, a nitrile group, a nitro group and an alkoxy group, and a halogen atom. Further, $R_5$, $R_6$, $R_7$ and $R_8$ may bind with each other to form a ring. In addition, a precursor of a mercapto group indicates a mercapto group-producing precursor, for example, such as thiazolidines, thioethers and disulfides.

Further, a cationic N-substituted nitrogen-containing aromatic compound used in the present invention does not contain a mercapto group and/or a precursor of a mercapto group. In addition, a ring containing a nitrogen atom in the cationic N-substituted nitrogen-containing aromatic compound represents preferably a 3- to 8-membered ring, and more preferably a 5- to 7-membered ring. In addition, this compound may be a monocyclic compound or a polycyclic compound having a condensed ring, and the number of nitrogen atoms may be one, or 2 or more. The cationic N-substituted nitrogen-containing aromatic compound includes, for example, a compound having a pyridine ring and a compound having a quinoline ring, and preferably used are an N-methylpyridinium salt, a cetylpyridinium salt, a dodecylpyridinium salt, an N-methylquinolinium salt, an N-ethylquinolinium salt, etc.

In addition, in the method for preparing bisphenol by reacting phenol compounds with ketone, at least one kind of cationic compound selected from compounds represented by the formulae (1), (2) and (3) and an N-substituted nitrogen-containing aromatic compound, may contain an amide bond.

The modified acidic ion-exchange resin in the present invention may use at least one kind of cationic compound selected from compounds represented by the formulae (1), (2) and (3) and an N-substituted nitrogen-containing aromatic compound, alone or in a combination of two or more. Further, it may be partially neutralized with a cation other than at least one kind of cationic compound selected from compounds represented by the formulae (1), (2) and (3) and an N-substituted nitrogen-containing aromatic compound, such as an ammonium cation and a metal cation.

In the preparation of the modified acidic ion-exchange resin catalyst in the present invention, at least one kind of cationic compound selected from compounds represented by the formulae (1), (2) and (3) and an N-substituted nitrogen-containing aromatic compound, may ionically bind with a functional group, just before use in the reaction. Thus, the modified acidic ion-exchange resin catalyst may be prepared by using the cationic compound and/or the cationic N-substituted nitrogen-containing aromatic compound in such a state, directly or the precursors thereof. The modification method is not particularly limited. For example, as a simple and easy method, it may use a method for dissolving them in a solvent such as water and an organic solvent to be brought into contact with a liquid phase, and in the case of using a volatile material, it may be brought into contact with an ion-exchange resin in a gas phase to modify the resin. Further, there may be used a method for consequently yielding a form of a modified acidic ion-exchange resin, wherein an equivalent weight or an excessive amount of a cationic compound or a precursor thereof is used to neutralize an ion-exchange resin, and then the ion-exchange resin is brought into contact with an acidic solution to be returned to be a partially acidic type, or the like.

For an acidic ion-exchange resin, the resin which contains a sulfonic acid group can be preferably used. The modified amount of the modified acidic ion-exchange resin catalyst in the present invention is 1 to 50% of the total sulfonic acid groups. By this, it is possible to express the modification effect to a maximum degree without remarkably decreasing the activity due to the decrease in an acid amount.

The acid amount in an ion-exchange resin can be calculated by a general exchange capacity measurement of an acidic ion-exchange resin. In the present invention, 0.2 g of a dry resin was stirred in 200 ml of an aqueous 10% NaCl solution for 1 hour, and the total amount of the filtrate was titrated with an aqueous 0.05 N NaOH solution to obtain a titration curve from which the acid amount was determined.

A reaction for preparing bisphenol A essentially proceeds with only an acid catalyst, but usually a method to improve the catalytic activity and the selectivity by making a mercapto group-containing compound coexist as a cocatalyst. In the present invention, it is preferable to make a mercapto group-containing compound coexist. Such a method includes a method wherein a mercapto group-containing compound such as alkyl mercaptan is mixed in a small amount with a mixture of phenol and acetone which are raw materials, and the resultant mixture is used, and a method wherein a mercapto group-containing compound binds to an acidic functional group of an acidic ion-exchange resin, and any of such methods may be used. Also, both of the method for mixing the compound with raw materials and the method for binding the compound to the acidic functional group may be used at a time.

A mercapto group-containing compound which is mixed with a mixture of phenol and acetone, is not particularly limited to other structures, if it contains a mercapto group in a molecule. It includes, for example, mercaptoalkyl groups such as a mercaptomethyl group, a 2-mercaptoethyl group, and a 3-mercapto-n-propyl group; alicyclic hydrocarbon groups such as a 4-mercaptocyclohexyl group and a 4-mercaptomethylcyclohexyl group; and mercaptoaromatic groups such as a p-mercaptophenyl group and a p-mercaptomethylphenyl group. Further, these aromatic, or aliphatic or alicyclic hydrocarbon groups may be hydrocarbon groups having a substituent such as a halogen atom, an alkoxy group, a nitro group, and a hydroxyl group, in addition to a mercapto group. The amount of the mercapto group-containing compound added to the mixture of phenol and acetone is preferably in the range of 100 ppm by weight to 5% by weight. By this, it is possible to exhibit the cocatalytic effect to a maximum degree with a small amount of a cocatalyst.

A mercapto group-containing compound which binds to a portion of acidic functional groups of an acidic ion-exchange resin, is not particularly limited, if it is a compound which ionically binds with the acidic functional group of the acidic ion-exchange resin. Such a compound includes mercaptoalkylamines such as 2-mercaptoethylamine (cysteamine), 3-mercaptopropylamine, and N,N-dimethyl-3-mercaptopropylamine; mercaptoalkylpyridines such as 3-mercaptomethylpyridine, 3-mercaptoethylpyridine, and 4-mercaptoethylpyridine; and thiazolidines such as thiazolidine, 2,2-dimethylthiazolidine, 2-methyl-2-phenylthiazolidine, and 3-methylthiazolidine. The ratio of a mercapto group-containing compound to bind with an acidic functional group is 0.5 to 70%, and preferably 5 to 30% of the total sulfonic acid groups of the sulfonic acid-type cation-exchange resin. By this, it is possible to exhibit the cocatalytic effect to a maximum degree without causing the decrease in the activity due to the decrease in an acid amount. For a method wherein a mercapto group-containing compound binds to an acidic ion-exchange resin, there may be used a conventionally known method as disclosed in Japanese Examined Patent Application Publication No. 46-19953, etc.

In the present invention, for phenol to be used as a raw material for preparing bisphenol A, a usually available technical phenol can be used. Industrial Phenol includes ones obtained by a cumene method, a toluene oxidation method, etc., any of which can be used. Generally, phenol having a purity of 98% or more is commercially available. Such an industrial phenol as it is may be used in the synthesis reaction of bisphenol A, but preferably phenol which is preliminarily treated with a strong acid-type cation-exchange resin in a continuous reaction or in a batch reaction before carrying out the reaction at a treatment temperature of 50 to 120° C. during a contact time of 5 minutes to 10 hours, and then the acetone-derived carbonyl compounds are removed, is used. Even more preferably, phenol which is brought into contact with a strong acid-type cation-exchange resin and then is subjected to a distillation treatment at a normal pressure to under reduced pressure of 10 mmHg at a temperature of 70 to 200° C., is used.

Acetone to be used in the present invention is not particularly limited, but it is commercially industrial acetone which is usually available. Generally, acetone having a purity of 99% or more is available.

The amounts (quantitative ratio) of phenol and acetone used as raw materials, are not particularly limited, but the molar ratio of phenol/acetone is recommended in the range of 0.1 to 100, and more preferably in the range of 0.5 to 50. If the amount of phenol is extremely small, it is difficult to accomplish a high conversion of acetone as a raw material. While the amount of phenol is too large, the reactor becomes unreasonably larger because phenol is used in the higher amount than required, and massive circulation of phenol is also required, although a high conversion of acetone can be accomplished. Thus, an efficient preparation cannot be accomplished.

In addition, as described in EP 583712, a mixture of these raw materials may include 1% or less of moisture beforehand.

In the present invention, the reaction temperature is not particularly limited, but it is preferably in the range of 0 to 300° C., and more preferably in the range of 30 to 200° C. If the reaction temperature is extremely low, the reaction rate decreases and the productivity of a reaction product also decreases. On the other hand, if the reaction temperature is extremely high, an undesirable side reaction, etc. proceeds, thus leading to the increase in the amount of by-products, and to the decrease in the stability of phenol as a raw material or bisphenol A as a product, and the reaction selectivity. Therefore, it is not economical.

The reaction can be carried out under reduced pressure, under applied pressure, or at normal pressure. In view of the reaction efficiency (the reaction efficiency per unit volume), it is not preferable to carry out the reaction under too low pressure. Usually, the pressure for carrying out the reaction is preferably in the range of 0.1 to 200 atm, and more preferably in the range of 0.5 to 100 atm. Of course, the present invention is not limited to such pressure ranges.

In addition, when carrying out the present invention, the amount of the catalyst used is not particularly limited, but for example; when carrying out the reaction in batch, it is recommended to carry out the invention such that the amount of the catalyst is preferably in the range of 0.001 to 200% by weight, and more preferably in the range of 0.1 to 50% by weight with respect to phenol.

When carrying out the present invention, it is possible to add a solvent or gas which is inert to a catalyst and a reaction reagent in the reaction system, which can be used in the diluted state. Specifically, aliphatic hydrocarbons such as methane, ethane, propane, butane, hexane, and cyclohexane, and an inert gas such as nitrogen, argon, and helium, if necessary, a hydrogen atom can be used as a diluent.

When carrying out the present invention, the method can be carried out in batch, semi-batch or continuous flow system. It can be carried out in any of a liquid phase, a gas phase, a gas-liquid mixed phase. Preferably, in view of the reaction efficiency, it is recommended that the reaction is carried out in the liquid phase. For a way for charging a catalyst, various kinds of ways using, for example, a fixed bed, a fluidized bed, a suspended bed and a plate fixed bed can be employed, any of which can be used.

The reaction time (retention time or catalytic contact time in the flow system) is not particularly limited, but it is usually 0.1 second to 30 hours, and preferably 0.5 second to 15 hours. After the completion of reaction, the reaction product can be separated and recovered from the catalysts, etc. by a separation method such as filtration, extraction, distilling-off. Bisphenol A as a target product can be separated from the reaction mixture and can be obtained by separation and purification by performing a sequential treatment of solvent extraction, distillation, alkali treatment and acid treatment, or an ordinary separation and purification method suitably combining them. In addition, unreacted raw materials can be recovered and recycled into the reaction system for use.

In the case of a batch reaction, the catalyst which is separated and recovered from the reaction product after reaction, can be used as it is, or partially or wholly reproduced to be repeatedly used for the reaction. When carrying out the reaction in a fixed bed or a fluidized bed flow system, the catalyst can be provided to the reaction, and further if a part or all of the catalysts is inactivated or is deteriorated in the activity, the reaction can be stopped to reproduce the catalyst, which can be provided to the reaction. Alternatively, a part of the catalyst can be withdrawn continuously or intermittently and reproduced, and then recycled to the reactor for re-use. Further, a fresh catalyst can be intermittently supplied to the reactor. When carrying out the reaction in a moving-bed flow system, the catalyst can be separated, recovered and, if necessary, reproduced, as in the batch reaction.

The catalyst may be reproduced by any method, for example, washing with water or an organic solvent, or further modifying after washing with an acidic solution, provided that the catalyst performance is restored. Further, the catalyst may be several times washed with an acidic solution and an alkaline solution alternately, and finally with an acidic solution, and then be modified.

EXAMPLES

Hereinbelow, the present invention will be described in more detail with reference to Examples. However, the present invention is not intended to be limited to Examples.

Example 1

(1) Preparation of a Modified Ion-Exchange Resin Catalyst

While vigorously stirring the water-swollen Amberlyst 31 (dry weight 4 g) with 80 ml of ion-exchange water, thereto was slowly added dropwise 40 ml of an aqueous n-tetrabutylammonium chloride solution having a concentration of 0.153 mole/L. After completing the dropwise addition, the mixture was further stirred for 5 hours, and was then repeatedly filtered and washed with ion-exchange water. Thereafter, it was dried under vacuum at 80° C. for 10 hours or longer to obtain Catalyst 1. The results of the measurement of an acid amount and of the elemental analysis in the Catalyst are shown in Table 1.

(2) Synthesis Reaction of Bisphenol A 6.63 g of phenol, 0.37 g of acetone and 0.35 g of Catalyst 1 prepared in (1), were put into a 70 ml pressure-resistant reactor, and 3-mercaptopropionic acid was put thereto such that the concentration is 3000 ppm. Then, the pressure-resistant reactor was pressurized with nitrogen gas under 5 kg/cm² gauge pressure, and was stirred with heating at 75° C. for 2 hours to perform the reaction. After completing the reaction, it was cooled to room temperature. After pressure discharge, the reaction solution was taken out, and was subjected to quantitative analysis by means of liquid chromatography. The results were shown in Table 2.

Example 2

In the same manner as in (1) of Example 1, except that an aqueous tetramethylammonium chloride solution having a concentration of 0.153 mole/L was used instead of an aqueous tetrabutylammonium chloride solution, the operation was performed to obtain Catalyst 2. The results of the measurement of an acid amount and of the elemental analysis in the Catalyst are shown in Table 1. In addition, under the same conditions as in (2) of Example 1, except that Catalyst 2 was used instead of Catalyst 1, the synthesis reaction of bisphenol A was performed. The results were shown in Table 2.

Example 3

In the same manner as in (1) of Example 1, except that an aqueous n-dodecyltrimethylammonium chloride solution having a concentration of 0.153 mole/L was used instead of an aqueous tetrabutylammonium chloride solution, the operation was performed to obtain Catalyst 3. The results of the measurement of an acid amount and of the elemental analysis in the Catalyst are shown in Table 1. In addition, under the same conditions as in (2) of Example 1, except that Catalyst 3 was used instead of Catalyst 1, the synthesis reaction of bisphenol A was performed. The results were shown in Table 2.

Example 4

In the same manner as in (1) of Example 1, except that an aqueous hexamethonium chloride solution having a concentration of 0.077 mole/L was used instead of an aqueous tetrabutylammonium chloride solution, the operation was performed to obtain Catalyst 4. The results of the measurement of an acid amount and of the elemental analysis in the Catalyst are shown in Table 1. In addition, under the same conditions as in (2) of Example 1, except that Catalyst 4 was used instead of Catalyst 1, the synthesis reaction of bisphenol A was performed. The results were shown in Table 2.

Example 5

In the same manner as in (1) of Example 1, except that an aqueous cetylpyridinium chloride solution having a concentration of 0.153 mole/L was used instead of an aqueous tetrabutylammonium chloride solution, the operation was performed to obtain Catalyst 5. The results of the measurement of an acid amount and of the elemental analysis in the Catalyst are shown in Table 1. In addition, under the same conditions as in (2) of Example 1, except that Catalyst 5 was used instead of Catalyst 1, the synthesis reaction of bisphenol A was performed. The results were shown in Table 2.

Example 6

In the same manner as in (1) of Example 1, except that an aqueous tetrabutylphosphonium chloride solution having a concentration of 0.153 mole/L was used instead of an aqueous tetrabutylammonium chloride solution, the operation was performed to obtain Catalyst 6. The results of the measurement of an acid amount and of the elemental analysis in the Catalyst are shown in Table 1. In addition, under the same conditions as in (2) of Example 1, except that Catalyst 6 was used instead of Catalyst 1, the synthesis reaction of bisphenol A was performed. The results were shown in Table 2.

Example 7

In the same manner as in (1) of Example 1, except that an aqueous tetraphenylphosphonium chloride solution having a concentration of 0.153 mole/L was used instead of an aqueous tetrabutylammonium chloride solution, the operation was performed to obtain Catalyst 7. The results of the measurement of an acid amount and of the elemental analysis in the Catalyst are shown in Table 1. In addition, under the same conditions as in (2) of Example 1, except that Catalyst 7 was used instead of Catalyst 1, the synthesis reaction of bisphenol A was performed. The results were shown in Table 2.

Example 8

In the same manner as in (1) of Example 1, except that acetonitrile is used instead of ion-exchange water, and a 0.153 mole/L solution of hydroxymethyltriphenylphosphonium chloride in acetonitrile was used instead of an aqueous tetrabutylammonium chloride solution, the operation was performed to obtain Catalyst 8. The results of the measurement of an acid amount and of the elemental analysis in the Catalyst are shown in Table 1. In addition, under the same conditions as in (2) of Example 1, except that Catalyst 8 was used instead of Catalyst 1, the synthesis reaction of bisphenol A was performed. The results were shown in Table 2.

Example 9

In the same manner as in (1) of Example 1, except that a solution of bis(triphenylphosphoranylidene)ammonium chloride in ethanol having a concentration of 0.153 mole/L was used instead of an aqueous tetrabutylammonium chloride solution, the operation was performed to obtain Catalyst 9. The results of the measurement of an acid amount and of the elemental analysis in the Catalyst are shown in Table 1. In addition, under the same conditions as in (2) of Example 1, except that Catalyst 9 was used instead of Catalyst 1, the synthesis reaction of bisphenol A was performed. The results were shown in Table 2.

Example 10

In the same manner as in (1) of Example 1, except that an aqueous tetraethylphosphonium chloride solution having a concentration of 0.153 mole/L was used instead of an aqueous tetrabutylammonium chloride solution, the operation was performed to obtain Catalyst 10. The results of the measurement of an acid amount and of the elemental analysis in the Catalyst are shown in Table 1. In addition, under the same conditions as in (2) of Example 1, except that Catalyst 10 was used instead of Catalyst 1, the synthesis reaction of bisphenol A was performed. The results were shown in Table 2.

Example 11

In the same manner as in (1) of Example 1, except that acetonitrile is used instead of ion-exchange water, and a 0.153 mole/L solution of triphenylphosphine in acetonitrile was used instead of an aqueous tetrabutylammonium chloride solution, the operation was performed to obtain Catalyst 11. The results of the measurement of an acid amount and of the elemental analysis in the Catalyst are shown in Table 1. In addition, under the same conditions as in (2) of Example 1, except that Catalyst 11 was used instead of Catalyst 1, the synthesis reaction of bisphenol A was performed. The results were shown in Table 2.

Example 12

In the same manner as in (1) of Example 1, except that acetonitrile is used instead of ion-exchange water, and a solution of diphenylethoxyphosphine in acetonitrile having a concentration of 0.153 mole/L was used instead of an aqueous tetrabutylammonium chloride solution, the operation was performed to obtain Catalyst 12. The results of the measurement of an acid amount and of the elemental analysis in the catalyst are shown in Table 1. In addition, under the same conditions as in (2) of Example 1, except that Catalyst 12 was used instead of Catalyst 1, the synthesis reaction of bisphenol A was performed. The results were shown in Table 2.

Reference Example 1

In the same manner as in (1) of Example 1, except that an aqueous trimethylamine hydrochloride solution having a concentration of 0.153 mole/L was used instead of an aqueous tetrabutylammonium chloride solution, the operation was performed to obtain Catalyst 13. The results of the measurement of an acid amount and of the elemental analysis in the Catalyst are shown in Table 1. In addition, under the same conditions as in (2) of Example 1, except that Catalyst 13 was used instead of Catalyst 1, the synthesis reaction of bisphenol A was performed. The results were shown in Table 2.

Reference Example 2

In the same manner as in (1) of Example 1, except that an aqueous pyridine solution having a concentration of 0.153 mole/L was used instead of an aqueous tetrabutylammonium chloride solution, the operation was performed to obtain Catalyst 14. The results of the measurement of an acid amount and of the elemental analysis in the Catalyst are shown in Table 1. In addition, under the same conditions as in (2) of Example 1, except that Catalyst 14 was used instead of Catalyst 1, the synthesis reaction of bisphenol A was performed. The results were shown in Table 2.

Comparative Example 1

Under the same conditions as in (2) of Example 1, except that sufficiently dried Amberlyst 31 which is commercially available, was used instead of Catalyst 1, the reaction was performed. The results were shown in Table 2. In addition, the results of the measurement of an acid amount and of the elemental analysis of a commercially available Amberlyst 31, are shown in Table 1.

Comparative Example 2

In the same manner as in (1) of Example 1, except that an aqueous ammonia solution having a concentration of 0.153 mole/L was used instead of an aqueous tetrabutylammonium chloride solution, the operation was performed to obtain Catalyst 15. The results of the measurement of an acid amount and of the elemental analysis of the catalyst are shown in Table 1. In addition, under the same conditions as in (2) of Example 1, except that Catalyst 15 was used instead of Catalyst 1, the synthesis reaction of bisphenol A was performed. The results were shown in Table 2.

Example 13

6.50 g of phenol, 0.50 g of acetone and 0.35 g of (1) the prepared Catalyst 1, were put into a 70 ml pressure-resistant reactor, and 3-mercaptopropionic acid was put thereto such that the concentration is 3000 ppm. Then, the pressure-resistant reactor was pressurized with nitrogen gas under 5 kg/cm² gauge pressure, and was stirred with heating at 85° C. for 2 hours to perform the reaction. After completing the reaction, it was cooled to room temperature. After pressure discharge, the reaction solution was taken out, and was subjected to quantitative analysis by means of liquid chromatography. The results were shown in Table 2.

Comparative Example 3

Under the same conditions as in Example 12, except that a commercially available Amberlyst 31 which is sufficiently dried, was used instead of Catalyst 1, the synthesis reaction of bisphenol A was performed. The results were shown in Table 2.

Example 14

(1) Preparation of a Modified Ion-Exchange Resin Catalyst

While vigorously stirring the water-swollen Amberlyst 31 (dry weight 4 g) with 80 ml of ion-exchange water, thereto was slowly added dropwise 40 ml of a mixed aqueous solution of 0.077 mole/L of tetramethylammonium chloride and 0.077 mole/L of aminoethanethiol hydrochloride. After completing the dropwise addition, the mixture was further stirred for 5 hours, and was then repeatedly filtered and washed with ion-exchange water. Thereafter, it was dried under vacuum at 80° C. for 10 hours or longer to obtain Catalyst 16. The results of the measurement of an acid amount and of the elemental analysis in the Catalyst are shown in Table 1.

(2) Synthesis Reaction of Bisphenol A 6.63 g of phenol, 0.37 g of acetone and 0.35 g of Catalyst 16 prepared in (1) were put into a 70 ml pressure-resistant reactor. The pressure-resistant reactor was pressurized with nitrogen gas under 5 kg/cm² gauge pressure, and was stirred with heating at 75° C. for 2 hours to perform the reaction. After completing the reaction, it was cooled to room temperature. After pressure discharge, the reaction solution was taken out, and was subjected to quantitative analysis by means of liquid chromatography. The results were shown in Table 2.

Example 15

In the same manner as in (1) of Example 14, except that tetraphenylphosphonium chloride was used instead of tetramethylammonium chloride, the operation was performed to obtain Catalyst 17. The results of the measurement of an acid amount and of the elemental analysis in the Catalyst are shown in Table 1. In addition, under the same conditions as in (2) of Example 14, except that Catalyst 17 was used instead of Catalyst 16, the synthesis reaction of bisphenol A was performed. The results were shown in Table 2.

Example 16

(1) Preparation of a Modified Ion-Exchange Resin Catalyst

While vigorously stirring the water-swollen Amberlyst 31 (dry weight 4 g) with 80 ml of ion-exchange water, thereto was slowly added dropwise 40 ml of a 0.077 mole/L solution of hydroxymethyltriphenylphosphonium chloride in acetonitrile. After completing the dropwise addition, the mixture was further stirred for 5 hours, and was then repeatedly filtered and washed with ion-exchange water. Thereafter, it was dried under vacuum at 80° C. for 10 hours or longer to obtain a solid. The obtained solid was dispersed in 80 mL of ion-exchange water, and thereto was slowly added dropwise 40 ml of an aqueous 0.077 mole/L aminoethanethiol hydrochloride solution with stirring. After completing the dropwise addition, the mixture was continuously stirred for 5 hours, and was then repeatedly filtered and washed with ion-exchange water. Thereafter, it was dried under vacuum at 80° C. for 10 hours or longer to obtain Catalyst 18. The results of the measurement of an acid amount and of the elemental analysis in the Catalyst are shown in Table 1.

(2) Synthesis Reaction of Bisphenol A

Under the same conditions as in (2) of Example 14, except that Catalyst 18 was used instead of Catalyst 16, the synthesis reaction of bisphenol A was performed. The results were shown in Table 2.

Example 17

In the same manner as in (1) of Example 14, except that tetraethylphosphonium chloride was used instead of tetramethylammonium chloride, the operation was performed to obtain Catalyst 19. The results of the measurement of an acid amount and of the elemental analysis of the Catalyst are shown in Table 1. In addition, under the same conditions as in (2) of Example 14, except that Catalyst 19 was used instead of Catalyst 16, the synthesis reaction of bisphenol A was performed. The results were shown in Table 2.

Example 18

In the same manner as in (1) of Example 14, except that cetylpyridinium chloride was used instead of tetramethylammonium chloride, the operation was performed to obtain Catalyst 20. In addition, under the same conditions as in (2) of Example 14, except that Catalyst 20 was used instead of Catalyst 16, the synthesis reaction of bisphenol A was performed. The results were shown in Table 2.

Example 19

In the same manner as in (1) of Example 16, except that triphenylphosphine was used instead of hydroxymethyltriphenylphosphonium chloride, the operation was performed to obtain Catalyst 21. The results of the measurement of an acid amount and of the elemental analysis in the Catalyst are shown in Table 1. In addition, under the same conditions as in (2) of Example 14, except that Catalyst 21 was used instead of Catalyst 16, the synthesis reaction of bisphenol A was performed. The results were shown in Table 2.

Example 20

In the same manner as in (1) of Example 16, except that diphenylethoxyphosphine was used instead of hydroxymethyltriphenylphosphonium chloride, the operation was performed to obtain Catalyst 22. The results of the measurement of an acid amount and of the elemental analysis in the Catalyst are shown in Table 1. In addition, under the same conditions as in (2) of Example 14, except that Catalyst 22 was used instead of Catalyst 16, the synthesis reaction of bisphenol A was performed. The results were shown in Table 2.

Reference Example 3

In the same manner as in (1) of Example 14, except that pyridine was used instead of tetramethylammonium chloride, the operation was performed to obtain Catalyst 23. The results of the measurement of an acid amount and of the elemental analysis in the Catalyst are shown in Table 1. In addition, under the same conditions as in (2) of Example 14, except that Catalyst 23 was used instead of Catalyst 16, the synthesis reaction of bisphenol A was performed. The results were shown in Table 2.

Reference Example 4

In the same manner as in (1) of Example 14, except that trimethylamine hydrochloride was used instead of tetramethylammonium chloride, the operation was performed to obtain Catalyst 24. The results of the measurement of an acid amount and of the elemental analysis in the Catalyst are shown in Table 1. In addition, under the same conditions as in (2) of Example 14, except that Catalyst 24 was used instead of Catalyst 16, the synthesis reaction of bisphenol A was performed. The results were shown in Table 2.

Comparative Example 4

While vigorously stirring the water-swollen Amberlyst 31 (dry weight 4 g) with 80 ml of ion-exchange water, thereto was slowly added dropwise 40 ml of an aqueous 0.077 mole/L aminoethanethiol hydrochloride solution. After completing the dropwise addition, the mixture was further stirred for 5 hours, and was then repeatedly filtered and washed with ion-exchange water. Thereafter, it was dried under vacuum at 80° C. for 10 hours or longer to obtain Catalyst 25. The results of the measurement of an acid amount and of the elemental analysis in the Catalyst are shown in Table 1.

In addition, under the same conditions as in (2) of Example 14, except that Catalyst 25 was used instead of Catalyst 16, the synthesis reaction of bisphenol A was performed. The results were shown in Table 2.

Example 21

(1) Preparation of a Modified Ion-Exchange Resin Catalyst

While vigorously stirring the water-swollen Amberlyst 31 (dry weight 4 g) with 80 ml of ion-exchange water, thereto was slowly added dropwise 40 ml of an aqueous mixed solution of 0.077 mole/L of tetramethylammonium chloride and 0.077 mole/L of 4-pyridineethanethiol hydrochloride. After completing the dropwise addition, the mixture was further stirred for 5 hours, and was then repeatedly filtered and washed with ion-exchange water. Thereafter, it was dried under vacuum at 80° C. for 10 hours or longer to obtain Catalyst 26. The results of the measurement of an acid amount and of the elemental analysis in the Catalyst are shown in Table 1.

(2) Synthesis Reaction of Bisphenol A 6.63 g of phenol, 0.37 g of acetone and 0.35 g of Catalyst 26 prepared in (1) were put into a 70 ml pressure-resistant reactor. The pressure-resistant reactor was pressurized with nitrogen gas under 5 kg/cm$^2$ gauge pressure, and was stirred with heating at 75° C. for 2 hours to perform the reaction. After completing the reaction, it was cooled to room temperature. After pressure discharge, the reaction solution was taken out, and was subjected to quantitative analysis by means of liquid chromatography. The results were shown in Table 2.

Example 22

In the same manner as in (1) of Example 21, except that tetraphenylphosphonium chloride was used instead of tetramethylammonium chloride, the operation was performed to obtain Catalyst 27. The results of the measurement of an acid amount and of the elemental analysis in the Catalyst are shown in Table 1. In addition, under the same conditions as in (2) of Example 21, except that Catalyst 27 was used instead of Catalyst 26, the synthesis reaction of bisphenol A was performed. The results were shown in Table 2.

Example 23

(1) Preparation of a Modified Ion-Exchange Resin Catalyst

While vigorously stirring the water-swollen Amberlyst 31 (dry weight 4 g) with 80 ml of acetonitrile, thereto was slowly added dropwise 40 ml of a 0.077 mole/L solution of hydroxymethyltriphenylphosphonium chloride in acetonitrile. After completing the dropwise addition, the mixture was further stirred for 5 hours, and was then repeatedly filtered and washed with ion-exchange water. Thereafter, it was dried under vacuum at 80° C. for 10 hours or longer. The obtained solid was dispersed in 80 mL of ion-exchange water, and thereto was slowly added dropwise 40 ml of an aqueous 0.077 mole/L 4-pyridineethanethiol hydrochloride solution with stirring. After completing the dropwise addition, the mixture was continuously stirred for 5 hours, and was then repeatedly filtered and washed with ion-exchange water. Thereafter, it was dried under vacuum at 80° C. for 10 hours or longer to obtain Catalyst 28. The results of the measurement of an acid amount and of the elemental analysis in the Catalyst are shown in Table 1.

(2) Synthesis Reaction of Bisphenol A

Under the same conditions as in (2) of Example 21, except that Catalyst 28 was used instead of Catalyst 26, the synthesis reaction of bisphenol A was performed. The results were shown in Table 2.

Example 24

In the same manner as in (1) of Example 21, except that tetraethylphosphonium chloride was used instead of tetramethylammonium chloride, the operation was performed to obtain Catalyst 29. The results of the measurement of an acid amount and of the elemental analysis in the Catalyst are shown in Table 1. In addition, under the same conditions as in (2) of Example 21, except that Catalyst 29 was used instead of Catalyst 26, the synthesis reaction of bisphenol A was performed. The results were shown in Table 2.

Example 25

In the same manner as in (1) of Example 21, except that cetylpyridinium chloride was used instead of tetramethylammonium chloride, the operation was performed to obtain Catalyst 30. The results of the measurement of an acid amount and of the elemental analysis in the Catalyst are shown in Table 1. In addition, under the same conditions as in (2) of Example 21, except that Catalyst 30 was used instead of Catalyst 26, the synthesis reaction of bisphenol A was performed. The results were shown in Table 2.

Example 26

In the same manner as in (1) of Example 23, except that triphenylphosphine was used instead of hydroxymethyltriphenylphosphonium chloride, the operation was performed to obtain Catalyst 31. The results of the measurement of an acid amount and of the elemental analysis in the Catalyst are shown in Table 1. In addition, under the same conditions as in (2) of Example 21, except that Catalyst 31 was used instead of Catalyst 26, the synthesis reaction of bisphenol A was performed. The results were shown in Table 2.

Example 27

In the same manner as in (1) of Example 23, except that diphenylethoxyphosphine was used instead of hydroxymethyltriphenylphosphonium chloride, the operation was performed to obtain Catalyst 32. The results of the measurement of an acid amount and of the elemental analysis in the Catalyst are shown in Table 1. In addition, under the same conditions as in (2) of Example 21, except that Catalyst 32 was used instead of Catalyst 26, the synthesis reaction of bisphenol A was performed. The results were shown in Table 2.

Reference Example 5

In the same manner as in (1) of Example 21, except that pyridine was used instead of tetramethylammonium chloride, the operation was performed to obtain Catalyst 33. The results of the measurement of an acid amount and of the elemental analysis in the Catalyst are shown in Table 1. In addition, under the same conditions as in (2) of Example 21, except that Catalyst 33 was used instead of Catalyst 26, the synthesis reaction of bisphenol A was performed. The results were shown in Table 2.

Reference Example 6

In the same manner as in (1) of Example 21, except that trimethylamine hydrochloride was used instead of tetramethylammonium chloride, the operation was performed to obtain Catalyst 34. The results of the measurement of an acid amount and of the elemental analysis in the Catalyst are shown in Table 1. In addition, under the same conditions as in (2) of Example 21, except that Catalyst 34 was used instead of Catalyst 26, the synthesis reaction of bisphenol A was performed The results were shown in Table 2.

Comparative Example 5

While vigorously stirring the water-swollen Amberlyst 31 (dry weight 4 g) with 80 ml of ion-exchange water, thereto was slowly added dropwise 40 ml of an aqueous 0.077 mole/L 4-pyridineethanethiol hydrochloride solution. After completing the dropwise addition, the mixture was further stirred for 5 hours, and was then repeatedly filtered and washed with ion-exchange water. Thereafter, it was dried under vacuum at 80° C. for 10 hours or longer to obtain Catalyst 35. The results of the measurement of an acid amount and of the elemental analysis in the Catalyst are shown in Table 1.

In addition, under the same conditions as in (2) of Example 21, except that Catalyst 35 was used instead of Catalyst 26, the synthesis reaction of bisphenol A was performed. The results were shown in Table 2.

Example 28

3.5 g of Catalyst 2 was filled with a cylindrical reactor (inside diameter: 21.4 mm, length: 470 mm). From the bottom of the reactor, the raw material solution to which was added 3-mercaptopropionic acid was supplied into the mixture of phenol/acetone having a molar ratio of 6:1 such that the concentration was 3000 ppm to proceed the synthesis reaction of bisphenol A at a reaction temperature of 85° C. When the amount of the flowing acetone reached 7 g, the amount of the supplied raw material solution was set such that the acetone conversion was about 65%, and then was fixed. When the amount of the flowing acetone was 7 g and 200 g, respectively, the reaction product was analyzed by liquid chromatography to determine the reduced levels of the acetone conversion and the selectivity to p,p'-bisphenol A, respectively. The results were shown in Table 3.

In addition, [Reduced level of conversion (%)]=[Conversion (%) when the amount of the flowing acetone is 7 g]−[Conversion (%) when the amount of the flowing acetone is 200 g], [Reduced level of selectivity (%)]=[Selectivity (%) when the amount of the flowing acetone is 7 g]−[Selectivity (%) when the amount of the flowing acetone is 200 g], and the followings were also calculated in this manner.

Example 29

The synthesis reaction of bisphenol A was performed under the same conditions as in Example 28, except that Catalyst 5 was used instead of Catalyst 2 to determine the reduced levels of the acetone conversion and the selectivity to p,p'-bisphenol A, respectively. The results were shown in Table 3.

Example 30

The synthesis reaction of bisphenol A was performed under the same conditions as in Example 28, except that Catalyst 7 was used instead of Catalyst 2 to determine the reduced levels of the acetone conversion and the selectivity to p,p'-bisphenol A, respectively. The results were shown in Table 3.

Example 31

The synthesis reaction of bisphenol A was performed under the same conditions as in Example 28, except that Catalyst 10 was used instead of Catalyst 2 to determine the reduced levels of the acetone conversion and the selectivity to p,p'-bisphenol A, respectively. The results were shown in Table 3.

Example 32

The synthesis reaction of bisphenol A was performed under the same conditions as in Example 28, except that Catalyst 11 was used instead of Catalyst 2 to determine the reduced levels of the acetone conversion and the selectivity to p,p'-bisphenol A, respectively. The results were shown in Table 3.

Example 33

The synthesis reaction of bisphenol A was performed under the same conditions as in Example 28, except that Catalyst 12 was used instead of Catalyst 2 to determine the reduced levels of the acetone conversion and the selectivity to p,p'-bisphenol A, respectively. The results were shown in Table 3.

Comparative Example 6

The synthesis reaction of bisphenol A was performed under the same conditions as in Example 28, except that Catalyst 13 was used instead of Catalyst 2 to determine the reduced levels of the acetone conversion and the selectivity to p,p'-bisphenol A, respectively. The results were shown in Table 3.

Comparative Example 7

The synthesis reaction of bisphenol A was performed under the same conditions as in Example 28, except that Catalyst 14 was used instead of Catalyst 2 to determine the reduced levels of the acetone conversion and the selectivity to p,p'-bisphenol A, respectively. The results were shown in Table 3.

Example 34

3.5 g of Catalyst 16 was filled with a cylindrical reactor (inside diameter: 21.4 mm, length: 470 mm). From the bottom of the reactor, the mixture of phenol/acetone having a molar ratio of 6:1 was supplied as a raw material solution to proceed the synthesis reaction of bisphenol A at a reaction temperature of 85° C. When the amount of the flowing acetone reached 7 g, the amount of the supplied raw material solution was set such that the acetone conversion was about 65%, and then was fixed. When the amount of the flowing acetone was 7 g and 200 g, respectively, the reaction product was analyzed by liquid chromatography to determine the reduced levels of the acetone conversion and the selectivity to p,p'-bisphenol A, respectively. The results were shown in Table 3.

Example 35

The synthesis reaction of bisphenol A was performed under the same conditions as in Example 34, except that Catalyst 17 was used instead of Catalyst 16 to determine the reduced levels of the acetone conversion and the selectivity to p,p'-bisphenol A, respectively. The results were shown in Table 3.

Example 36

The synthesis reaction of bisphenol A was performed under the same conditions as in Example 34, except that Catalyst 18 was used instead of Catalyst 16 to determine the reduced levels of the acetone conversion and the selectivity to p,p'-bisphenol A, respectively. The results were shown in Table 3.

Example 37

The synthesis reaction of bisphenol A was performed under the same conditions as in Example 34, except that Catalyst 19 was used instead of Catalyst 16 to determine the reduced levels of the acetone conversion and the selectivity to p,p'-bisphenol A, respectively. The results were shown in Table 3.

Example 38

The synthesis reaction of bisphenol A was performed under the same conditions as in Example 34, except that Catalyst 20 was used instead of Catalyst 16 to determine the reduced levels of the acetone conversion and the selectivity to p,p'-bisphenol A, respectively. The results were shown in Table 3.

Example 39

The synthesis reaction of bisphenol A was performed under the same conditions as in Example 34, except that Catalyst 21 was used instead of Catalyst 16 to determine the reduced levels of the acetone conversion and the selectivity to p,p'-bisphenol A, respectively. The results were shown in Table 3.

Example 40

The synthesis reaction of bisphenol A was performed under the same conditions as in Example 34, except that Catalyst 22 was used instead of Catalyst 16 to determine the reduced levels of the acetone conversion and the selectivity to p,p'-bisphenol A, respectively. The results were shown in Table 3.

Comparative Example 8

The synthesis reaction of bisphenol A was performed under the same conditions as in Example 34, except that Catalyst 23 was used instead of Catalyst 16 to determine the reduced levels of the acetone conversion and the selectivity to p,p'-bisphenol A, respectively. The results were shown in Table 3.

Comparative Example 9

The synthesis reaction of bisphenol A was performed under the same conditions as in Example 34, except that Catalyst 24 was used instead of Catalyst 16 to determine the reduced levels of the acetone conversion and the selectivity to p,p'-bisphenol A, respectively. The results were shown in Table 3.

Comparative Example 10

The synthesis reaction of bisphenol A was performed under the same conditions as in Example 34, except that Catalyst 25 was used instead of Catalyst 16 to determine the reduced levels of the acetone conversion and the selectivity to p,p'-bisphenol A, respectively. The results were shown in Table 3.

Example 41

3.5 g of Catalyst 26 was filled with a cylindrical reactor (inside diameter: 21.4 mm, length: 470 mm). From the bottom of the reactor, the mixture of phenol/acetone having a molar ratio of 6:1 was supplied as a raw material solution to proceed the synthesis reaction of bisphenol A at a reaction temperature of 85° C. When the amount of the flowing acetone reached 14 g, the amount of the supplied raw material solution was set such that the acetone conversion was about 65%, and then was fixed. When the amount of the flowing acetone was 14 g and 400 g, respectively, the reaction product was analyzed by liquid chromatography to determine the reduced levels of the acetone conversion and the selectivity to p,p'-bisphenol A, respectively. The results were shown in Table 3.

Example 42

The synthesis reaction of bisphenol A was performed under the same conditions as in Example 41, except that Catalyst 27 was used instead of Catalyst 26 to determine the reduced levels of the acetone conversion and the selectivity to p,p'-bisphenol A, respectively. The results were shown in Table 3.

Example 43

The synthesis reaction of bisphenol A was performed under the same conditions as in Example 41, except that Catalyst 28 was used instead of Catalyst 26 to determine the reduced levels of the acetone conversion and the selectivity to p,p'-bisphenol A, respectively. The results were shown in Table 3.

Example 44

The synthesis reaction of bisphenol A was performed under the same conditions as in Example 41, except that Catalyst 29 was used instead of Catalyst 26 to determine the reduced levels of the acetone conversion and the selectivity to p,p'-bisphenol A, respectively. The results were shown in Table 3.

Example 45

The synthesis reaction of bisphenol A was performed under the same conditions as in Example 41, except that Catalyst 30 was used instead of Catalyst 26 to determine the reduced levels of the acetone conversion and the selectivity to p,p'-bisphenol A, respectively. The results were shown in Table 3.

Example 46

The synthesis reaction of bisphenol A was performed under the same conditions as in Example 41, except that Catalyst 31 was used instead of Catalyst 26 to determine the reduced levels of the acetone conversion and the selectivity to p,p'-bisphenol A, respectively. The results were shown in Table 3.

Example 47

The synthesis reaction of bisphenol A was performed under the same conditions as in Example 41, except that Catalyst 32 was used instead of Catalyst 26 to determine the reduced levels of the acetone conversion and the selectivity to p,p'-bisphenol A, respectively. The results were shown in Table 3.

Comparative Example 11

The synthesis reaction of bisphenol A was performed under the same conditions as in Example 41, except that Catalyst 33 was used instead of Catalyst 26 to determine the reduced levels of the acetone conversion and the selectivity to p,p'-bisphenol A, respectively. The results were shown in Table 3.

Comparative Example 12

The synthesis reaction of bisphenol A was performed under the same conditions as in Example 41, except that Catalyst 34 was used instead of Catalyst 26 to determine the reduced levels of the acetone conversion and the selectivity to p,p'-bisphenol A, respectively. The results were shown in Table 3.

Comparative Example 13

The synthesis reaction of bisphenol A was performed under the same conditions as in Example 41, except that Catalyst 35 was used instead of Catalyst 26 to determine the reduced levels of the acetone conversion and the selectivity to p,p'-bisphenol A, respectively. The results were shown in Table 3.

TABLE 1

| | | | Catalyst | | | | | | | |
|---|---|---|---|---|---|---|---|---|---|---|
| | | Catalyst Acid Amount | Content of Carbon (%) | | Content of Nitrogen (%) | | Content of Phosphorus (%) | | Content of Sulfur (%) | |
| Example | Catalyst | (milliequivalents/g) | Found value | Theoretical value | Found value | Theoretical value | Found value | Theoretical value | Found value | Theoretical value |
| Ex. 1 | Cat. 1 | 2.73 | 62.0 | 62.3 | 1.5 | 1.5 | — | — | 11.4 | 11.6 |
| Ex. 2 | Cat. 2 | 3.48 | 56.9 | 57.1 | 1.5 | 1.6 | — | — | 14.0 | 14.3 |
| Ex. 3 | Cat. 3 | 2.96 | 61.2 | 61.5 | 1.4 | 1.4 | — | — | 11.8 | 12.1 |
| Ex. 4 | Cat. 4 | 3.19 | 57.7 | 58.0 | 1.3 | 1.4 | — | — | 13.8 | 14.0 |
| Ex. 5 | Cat. 5 | 2.62 | 64.0 | 64.2 | 1.4 | 1.4 | — | — | 10.7 | 11.0 |
| Ex. 6 | Cat. 6 | 2.70 | 60.8 | 61.1 | — | — | 3.0 | 3.2 | 11.1 | 11.4 |
| Ex. 7 | Cat. 7 | 2.47 | 65.5 | 65.7 | — | — | 2.7 | 3.0 | 10.4 | 10.5 |
| Ex. 8 | Cat. 8 | 2.68 | 62.2 | 62.5 | — | — | 2.7 | 3.0 | 11.0 | 11.2 |
| Ex. 9 | Cat. 9 | 2.11 | 66.4 | 66.7 | 1.1 | 1.1 | 4.6 | 4.9 | 8.8 | 8.9 |
| Ex. 10 | Cat. 10 | 3.06 | 57.6 | 57.9 | — | — | 3.4 | 3.6 | 12.7 | 12.9 |
| Ex. 11 | Cat. 11 | — | 63.4 | 63.6 | — | — | 3.1 | 3.3 | 11.0 | 11.2 |

TABLE 1-continued

| | | Catalyst | | | | | | | | |
|---|---|---|---|---|---|---|---|---|---|---|
| | | Catalyst Acid Amount | Content of Carbon (%) | | Content of Nitrogen (%) | | Content of Phosphorus (%) | | Content of Sulfur (%) | |
| Example | Catalyst | (milliequivalents/g) | Found value | Theoretical value | Found value | Theoretical value | Found value | Theoretical value | Found value | Theoretical value |
| Ex. 12 | Cat. 12 | — | 60.4 | 60.6 | — | — | 3.1 | 3.4 | 11.4 | 11.6 |
| Ref. Ex. 1 | Cat. 13 | 3.59 | 56.4 | 56.6 | 1.5 | 1.6 | — | — | 14.2 | 14.5 |
| Ref. Ex. 2 | Cat. 14 | 3.39 | 57.9 | 58.2 | 1.6 | 1.7 | — | — | 14.0 | 14.1 |
| Comp. Ex. 1 | Amberlyst 31 | 5.09 | 56.0 | 56.3 | — | — | — | — | 15.3 | 15.6 |
| Comp. Ex. 2 | Cat. 15 | 3.58 | 54.7 | 55.0 | 1.9 | 1.9 | — | — | 15.0 | 15.2 |
| Ex. 14 | Cat. 16 | 3.40 | 55.3 | 55.6 | 1.6 | 1.7 | — | — | 16.0 | 16.1 |
| Ex. 15 | Cat. 17 | 2.90 | 60.2 | 60.5 | 0.7 | 0.7 | 1.4 | 1.6 | 13.6 | 13.9 |
| Ex. 16 | Cat. 18 | 3.03 | 58.4 | 58.7 | 0.7 | 0.7 | 1.4 | 1.6 | 14.0 | 14.2 |
| Ex. 17 | Cat. 19 | 3.22 | 55.8 | 56.0 | 0.7 | 0.8 | 1.6 | 1.9 | 15.1 | 15.4 |
| Ex. 18 | Cat. 20 | 2.91 | 59.6 | 59.7 | 1.4 | 1.5 | — | — | 14.0 | 14.1 |
| Ex. 19 | Cat. 21 | — | 58.9 | 59.2 | 0.9 | 0.8 | 1.5 | 1.8 | 14.1 | 14.4 |
| Ex. 20 | Cat. 22 | — | 57.3 | 57.5 | 0.9 | 0.8 | 1.7 | 1.9 | 14.3 | 14.6 |
| Ref. Ex. 3 | Cat. 23 | 3.28 | 55.9 | 56.1 | 1.7 | 1.8 | — | — | 15.8 | 16.1 |
| Ref. Ex. 4 | Cat. 24 | 3.45 | 55.0 | 55.3 | 1.7 | 1.7 | — | — | 16.0 | 16.3 |
| Comp. Ex. 4 | Cat. 25 | 4.15 | 54.9 | 55.0 | 0.8 | 0.9 | — | — | 16.8 | 17.0 |
| Ex. 21 | Cat. 26 | 3.25 | 57.0 | 57.1 | 1.7 | 1.7 | — | — | 15.3 | 15.5 |
| Ex. 22 | Cat. 27 | 2.78 | 61.4 | 61.7 | 0.7 | 0.7 | 1.4 | 1.6 | 13.2 | 13.4 |
| Ex. 23 | Cat. 28 | 2.90 | 59.6 | 59.9 | 0.7 | 0.7 | 1.4 | 1.6 | 13.6 | 13.8 |
| Ex. 24 | Cat. 29 | 3.09 | 57.4 | 57.5 | 0.8 | 0.8 | 1.5 | 1.8 | 14.9 | 14.9 |
| Ex. 25 | Cat. 30 | 2.82 | 60.7 | 61.0 | 1.4 | 1.5 | — | — | 13.5 | 13.6 |
| Ex. 26 | Cat. 31 | — | 60.3 | 60.6 | 0.9 | 0.8 | 1.6 | 1.8 | 13.8 | 13.9 |
| Ex. 27 | Cat. 32 | — | 58.6 | 58.9 | 0.9 | 0.8 | 1.6 | 1.8 | 13.9 | 14.1 |
| Ref. Ex. 5 | Cat. 33 | 3.25 | 57.3 | 57.6 | 1.7 | 1.7 | — | — | 15.4 | 15.5 |
| Ref. Ex. 6 | Cat. 34 | 3.34 | 56.5 | 56.8 | 1.6 | 1.6 | — | — | 15.6 | 15.7 |
| Comp. Ex. 5 | Cat. 35 | 3.94 | 56.4 | 56.7 | 0.9 | 0.9 | — | — | 16.3 | 16.3 |

TABLE 2

| | Catalyst | Acetone Conversion (%) | Selectivity (%) to Bisphenol A |
|---|---|---|---|
| Ex. 1 | Catalyst 1 | 46.1 | 92.6 |
| Ex. 2 | Catalyst 2 | 64.8 | 92.8 |
| Ex. 3 | Catalyst 3 | 60.1 | 92.7 |
| Ex. 4 | Catalyst 4 | 46.1 | 92.5 |
| Ex. 5 | Catalyst 5 | 53.6 | 93.0 |
| Ex. 6 | Catalyst 6 | 43.9 | 92.9 |
| Ex. 7 | Catalyst 7 | 48.0 | 93.2 |
| Ex. 8 | Catalyst 8 | 56.8 | 93.3 |
| Ex. 9 | Catalyst 9 | 35.9 | 92.3 |
| Ex. 10 | Catalyst 10 | 63.0 | 93.1 |
| Ex. 11 | Catalyst 11 | 35.0 | 93.8 |
| Ex. 12 | Catalyst 12 | 41.2 | 93.4 |
| Ref. Ex. 1 | Catalyst 13 | 70.5 | 92.8 |
| Ref. Ex. 2 | Catalyst 14 | 66.6 | 93.2 |
| Comp. Ex. 1 | Amberlyst 31 | 81.9 | 91.5 |
| Comp. Ex. 2 | Catalyst 15 | 61.5 | 91.2 |
| Ex. 13 | Catalyst 1 | 45.2 | 89.7 |
| Comp. Ex. 3 | Amberlyst 31 | 77.9 | 87.3 |
| Ex. 14 | Catalyst 16 | 70.0 | 93.2 |
| Ex. 15 | Catalyst 17 | 53.1 | 93.3 |
| Ex. 16 | Catalyst 18 | 66.1 | 93.2 |
| Ex. 17 | Catalyst 19 | 68.0 | 93.3 |
| Ex. 18 | Catalyst 20 | 59.0 | 93.3 |
| Ex. 19 | Catalyst 21 | 64.1 | 94.0 |
| Ex. 20 | Catalyst 22 | 65.0 | 93.6 |
| Ref. Ex. 3 | Catalyst 23 | 73.4 | 93.3 |
| Ref. Ex. 4 | Catalyst 24 | 78.0 | 93.0 |
| Comp. Ex. 4 | Catalyst 25 | 87.0 | 92.3 |
| Ex. 21 | Catalyst 26 | 86.0 | 93.2 |
| Ex. 22 | Catalyst 27 | 63.9 | 93.0 |
| Ex. 23 | Catalyst 28 | 80.1 | 93.2 |
| Ex. 24 | Catalyst 29 | 84.3 | 93.1 |
| Ex. 25 | Catalyst 30 | 69.0 | 93.2 |
| Ex. 26 | Catalyst 31 | 74.0 | 93.5 |
| Ex. 27 | Catalyst 32 | 76.2 | 93.4 |
| Ref. Ex. 5 | Catalyst 33 | 88.1 | 93.4 |
| Ref. Ex. 6 | Catalyst 34 | 89.1 | 92.9 |
| Comp. Ex. 5 | Catalyst 35 | 92.3 | 91.5 |

TABLE 3

| | Reduced level of Conversion (%) | Reduced level of Selectivity (%) |
|---|---|---|
| Ex. 28 | 2.1 | 2.6 |
| Ex. 29 | 2.3 | 2.7 |
| Ex. 30 | 2.2 | 2.5 |
| Ex. 31 | 2.2 | 2.6 |
| Ex. 32 | 2.3 | 2.5 |
| Ex. 33 | 2.1 | 2.6 |
| Comp. Ex. 6 | 2.2 | 3.4 |
| Comp. Ex. 7 | 2.1 | 3.5 |

TABLE 3-continued

| | Reduced level of Conversion (%) | Reduced level of Selectivity (%) |
|---|---|---|
| Ex. 34 | 13.1 | 3.5 |
| Ex. 35 | 13.2 | 2.6 |
| Ex. 36 | 13.0 | 2.4 |
| Ex. 37 | 13.1 | 2.4 |
| Ex. 38 | 13.3 | 3.3 |
| Ex. 39 | 12.9 | 2.5 |
| Ex. 40 | 13.1 | 2.4 |
| Comp. Ex. 8 | 13.2 | 5.2 |
| Comp. Ex. 9 | 12.9 | 5.1 |
| Comp. Ex. 10 | 13.3 | 10.0 |
| Ex. 41 | 12.9 | 1.8 |
| Ex. 42 | 12.6 | 1.3 |
| Ex. 43 | 12.8 | 1.3 |
| Ex. 44 | 13.1 | 1.4 |
| Ex. 45 | 13.2 | 1.9 |
| Ex. 46 | 12.7 | 1.3 |
| Ex. 47 | 13.0 | 1.3 |
| Comp. Ex. 11 | 13.1 | 2.6 |
| Comp. Ex. 12 | 13.0 | 2.7 |
| Comp. Ex. 13 | 12.7 | 5.1 |

INDUSTRIAL APPLICABILITY

According to the method of the present invention, bisphenol can be prepared with a good yield and selectivity, and can be yielded with an excellent safety, process and economy.

The invention claimed is:

1. A method for preparing bisphenol comprising reacting phenol compounds with ketone and/or aldehyde, in the presence of a modified acidic ion-exchange resin which acts as a catalyst, wherein
   i) said modified acidic ion-exchange resin has at least one kind of cation selected from the group consisting of (A), (B), (C) and (D) ionically bound to an acidic functional group of an acidic ion-exchange resin, wherein the ratio of acidic functional groups modified with said cation is 0.1 to 50% of the total acidic functional groups of the acidic ion-exchange resin:
   (A) A cation represented by the formula (1):

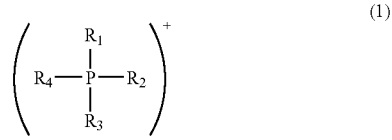

wherein P represents a phosphorus atom; and $R_1$, $R_2$, $R_3$ and $R_4$ independently represent a hydrogen atom, or an alkyl group, an aryl group or an alkoxy group, each of which contains 1 to 20 carbon atoms and may be substituted or unsubstituted and does not contain any of a mercapto group and a precursor thereof, provided that at least one of $R_1$, $R_2$, $R_3$ and $R_4$ is a group other than a hydrogen atom;

(B) A cation represented by the formula (2):

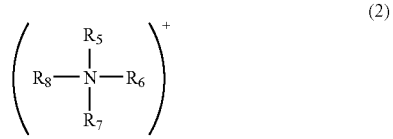

wherein N represents a nitrogen atom; and $R_5$, $R_6$, $R_7$ and $R_8$ independently represent an alkyl group or an aryl group, each of which contains 1 to 20 carbon atoms and may be substituted or unsubstituted and does not contain any of a mercapto group, a precursor thereof and an amide bond;

(C) A cation represented by the formula (3):

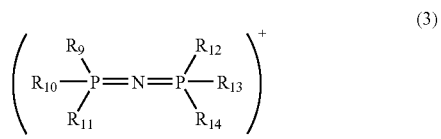

wherein P represents a phosphorus atom; and $R_9$, $R_{10}$, $R_{11}$, $R_{12}$, $R_{13}$ and $R_{14}$ independently represent a hydrogen atom, or an alkyl group, an aryl group or an alkoxy group, each of which contains 1 to 20 carbon atoms and may be substituted or unsubstituted and does not contain any of a mercapto group, a precursor thereof and an amide bond, provided that at least one of $R_9$, $R_{10}$, $R_{11}$, $R_{12}$, $R_{13}$ and $R_{14}$ is a group other than a hydrogen atom; and (D) A cation which does not contain any of a mercapto group, a precursor thereof and an amide bond, wherein said cation is a N-methylpyridinium salt, a N-cetylpyridinium salt, a N-dodecylpyridinium salt, a N-methylquinolinium salt or a N-ethylquinolinium salt, and ii-a) at least one compound containing a mercapto group is added to the mixture of reaction raw materials, wherein the amount of said compound is in the range of 100 ppm by weight to 5% by weight of the mixture, and/or ii-b) a nitrogen-containing compound containing a mercapto group, which is different from the compound containing a mercapto group of ii-a), further ionically binds to an acidic functional group of the acidic ion-exchange resin, wherein the ratio of acidic functional groups binding to said compound is 0.5 to 70% of the total acidic functional groups of the acidic ion-exchange resin.

2. The method for preparing bisphenol comprising reacting phenol compounds with ketone and/or aldehydes according to claim 1, wherein the nitrogen-containing compound containing a mercapto group of ii-b) is selected from the group consisting of a mercaptoalkylamine, a mercaptoalkylpyridine and a thiazolidine.

3. The method for preparing bisphenol comprising reacting phenol compounds with ketone and/or aldehydes according to claim 1, wherein the compound containing a mercapto group of ii-a) is selected from the group consisting of a compound containing a mercaptoalkyl group, a compound containing alicyclic hydrocarbon group and a compound containing mercaptoaromatic group.

4. The method for preparing bisphenol comprising reacting phenol compounds with ketone and/or aldehydes according to claim 1, wherein the compound containing a mercapto group of ii-a) is 3-mercaptopropionic acid.

* * * * *